United States Patent [19]

Jensenius

[11] Patent Number: 5,132,287
[45] Date of Patent: Jul. 21, 1992

[54] METHODS OF TREATING DISORDERS WHICH CAUSE CONGLUTININ DEFICIENCY

[75] Inventor: Jens C. Jensenius, Odense M, Denmark

[73] Assignee: Novo Industri A/S, Denmark

[21] Appl. No.: 441,792

[22] Filed: Nov. 27, 1989

Related U.S. Application Data

[62] Division of Ser. No. 939,112, Dec. 8, 1986, Pat. No. 4,906,134.

[30] Foreign Application Priority Data

Dec. 10, 1985 [DK] Denmark .............................. 5704/85

[51] Int. Cl.[5] ...................... A61K 37/46; A61K 37/02
[52] U.S. Cl. ...................................... 514/8; 424/85.8; 424/88; 514/2; 514/21
[58] Field of Search ...................... 424/86, 88, 89, 93; 514/2, 8, 21; 530/380, 381, 395, 808

[56] References Cited

U.S. PATENT DOCUMENTS

4,239,746 12/1980 Bartos et al.
4,342,566 8/1982 Theofilopoulos et al.
4,427,779 1/1984 Reckel et al.
4,503,035 3/1985 Pestka et al.
4,548,909 10/1985 Parratt.

FOREIGN PATENT DOCUMENTS

0022005 1/1981 European Pat. Off.
0155141 9/1985 European Pat. Off.
2333434 1/1975 Fed. Rep. of Germany.
82/01593 5/1982 PCT Int'l Appl.
2121417 12/1983 United Kingdom.

OTHER PUBLICATIONS

Coombs et al., "The Serology of Conglutinin and its Relation to Disease", Blackwell Sci. Pub., Oxford, Adler & Sons Ltd., Bartholomew Press, Dorking, (1961), pp. 46-50, 128-137 and 184-194.
Lachmann et al., J. Immunol., 100:691-698 (1968).
Hirani et al., J. Immunol., 134(2):1105-1109 (1985).
Ingram, D. G., (1972), "Biological Aspects of Conglutinin and Immunoconglutinins", Biological Activities of Complement, Kager, Basel, pp. 215-228.
Ingram, D. G., Immunol., 2:322-333 (1959a).
Ingram, D. G., Immunol., 2:334-335 (1959b).
Casali et al., Clin. Exp. Immunol., 37:295-309 (1979).
Barta et al., J. Immunol., 105:350 (1970).
Jonas et al., Vet. Immunol. Immunopathol., 5:289 (1983/1984).
Kawasaki et al., J. Biochem., 98:1309-1320 (1985).
Leon et al., Science, 143:1327-1328 (1964).
Linscott et al., J. Immunol., 121(2):658-664 (1978).
Stankiewicz et al., Archivum Immunologiae Therapiae Experimentalis, 33:423-428 (1985).
Strang et al., Biochem. J., 234:381-389 (1986).
Tlaskalova et al., Folia Microbiol., (Prague), 13:450-458 (1968).
Brown et al., J. Immunol., 128(2):860-865 (1982).
Lachmann et al., "Conglutinin and Immunoconglutinins", pp. 202-214 in Biological Activities of Complement, ed., D. G. Ingram, (Karger, Basel, 1972).
Coombs et al., J. Hyg. Camb., 48:484-499 (1950).
Lachmann et al., Immunology, 18:157-169 (1970).
Durand et al., J. Imm. Methods, 73:57-66 (1984).
Mittal et al., Immunology, 25:237-240 (1973).

(List continued on next page.)

Primary Examiner—Howard E. Schain
Attorney, Agent, or Firm—Sterne, Kessler, Goldstein & Fox

[57] ABSTRACT

Human conglutinin, polyclonal, and monoclonal antibodies raised against human conglutinin, and their uses in therapy and diagnosis are described.

Human conglutinin was obtained from human plasma by affinity chromatography with anti-bovine conglutinin antibody, has a relative molecular weight of 330 and 40 K unreduced and 66 K reduced as measured by SDS-PAGE, shows calcium-dependent and sugar inhibitable binding to complement-reacted immune complexes and zymosan, and immunological cross-reaction with anti-bovine conglutinin antibody.

6 Claims, 5 Drawing Sheets

OTHER PUBLICATIONS

Eisenberg et al., *J. Immunol.,* 118:1428–1434 (1977).
Jensenius et al., *Biosci. Rep.,* 5(10–11):901–5 (1985).
Eggert, *Biochem. Soc. Trans.,* 7:193–194 (1979).
Thiel et al., *Scand. J. Immunol.,* 26:461–468 (1987).
Sage et al., *J. Immunol.,* 90:347–357 (1963).
Lachmann et al., *Immunochemistry,* 1:37–41 (1964).
Eggert, *Int. Arch. Allergy Appl. Immun.,* 61:192–202 (1980).
Eggert, *Int. Arch. Allergy Appl. Immun.,* 61:203–212 (1980).
Eggert, *Int. Arch. Allergy Appl. Immun.,* 62:34–45 (1980).
Lachmann, *Adv. Immunol.,* 6:479–527 (1967).
Baatrup et al., *Scand. J. Immunol.,* 26:355–361 (1987).
Lachmann, *Immunology,* 5:687–705 (1962).
Davis et al., *Biochemistry,* 23:2139–2144 (1984).
Dunker et al., *J. Biol. Chem.,* 244:5047–5080 (1969).
Allison et al., *PNAS USA,* 75:3953–3956 (1978).
A copy of the European Search Report of the corresponding European Application No. 86 30 9595.
Ross et al., *J. Immunol.,* 134:3307–3315 (1985).
Tamura, *Biol. Abstracts,* 71:59809 (1980).
Hautanen et al., *Chem. Abstracts,* 92:56616x (1980).
Samuel et al., *Biol. Abstracts,* 82:111882 (1986).
Gupta et al., *Biol. Abstracts,* 73:32120 (1981).

METHODS OF TREATING DISORDERS WHICH CAUSE CONGLUTININ DEFICIENCY

CROSS-REFERENCES TO RELATED APPLICATIONS

This is a divisional of allowed co-pending application Ser. No. 939,112, filed Dec. 8, 1986, now U.S. Pat. No. 4,906,134, issued Mar. 6, 1990.

BACKGROUND OF THE INVENTION

1. Field of the Invention

This invention relates to human conglutinin, polyclonal and monoclonal anti-conglutinin antibody raised against human conglutinin, and their uses in therapy and diagnosis.

2. Description of Background Art

Conglutinin is the name given by Bordet and Streng (Zentr.Bakteriol.Parasitenk. Abt. 1 Orig. 49 (1909) pp. 260-276) to the component in bovine serum which induce the agglutination of erythrocytes coated with antibody and complement. Conglutinin was quite extensively studied at the beginning of this century and later reinvestigated by Coombs et al.: "The Serology of Conglutination and its Relation to Disease" (1961) Blackwell, Oxford, and Lachmann: Adv.Immunol. 6 (1967) pp. 479-527.

The activity was ascribed to a large, elongated protein molecule (Sage et al. J.Immunol. 90 (1963) pp. 347-357). More specifically, conglutinin was found to induce agglutination of erythrocytes exposing the C3 degradation product, iC3b. The C3b inactivating factor (Factor I) which splits the α-chain of C3b was thus originally named conglutinogen activation factor (or KAF) (Lachmann and Müller-Eberhard, J.Immunol. 100 (1968) pp. 691-698). Apparently, conglutinin shows no reactivity with native C3 or the further degraded fragments, C3dg or C3c. This has, however, lately been questioned since solid phase conglutinin in enzyme linked immunosorbent assays (ELISA) has been found to bind fluid phase C3c and C3b as well as iC3b (Hirani et al., J.Immunol. 134 (1985) pp. 1105-1109).

The physiological function of conglutinin remains hitherto unknown. Studies in bovidae have revealed that the content of conglutinin in blood decreases during infection and at parturition (Ingram D. G. "Biological aspects of conglutinin and immunoconglutinins, pp. 215-228 in D. A. Ingram Ed. "Biological Activities of Complement" Karger, Basel, Switzerland).

Conglutinin shows protective activity against bacterial infections as shown by Ingram D.G. (Immunology 2, 322-333, 1959 and Immunology 2, 334-345, 1959) in experiments where mice could be protected by the injection of bovine conglutinin in the form of a euglobulin precipitate from normal bovine serum redissolved in saline before the injection of pathogenic bacteria. This indicates that conglutinin is of importance for the non-specific immunity.

Conglutinin's binding of complement solubilized immune complexes has attracted interest. Immune complex assays based on this activity are popular and solid phase bovine conglutinin has been used to purify soluble circulating immune complexes (Casali and Lambert, Clin.Exp.Immunol. 37 (1979) pp. 295-309).

Conglutinin may be classified as a lectin on the basis of its reactivity with carbohydrates.

Attempts at demonstrating conglutinin in other species than the bovidae has generally failed (Davis and Lachmann, Biochemistry 23 (1984) p. 2139). However, some authors have claimed indications for the existence of conglutinin in swine (Barta et al., J.Immunol. 105 (1970) p. 350), and in sheep (Jonas and Stankiewiecz, Veterinary Immunology and Immunopathology 5 (1983/84 p. 289).

Despite considerable efforts the only possible analogue in the human so far described is the iC3b receptor (CR3) (Ross et al., J.Immunol. 134 (1985) pp. 3307-3315), which shows no structural homology to bovine conglutinin.

By employing functional and immunochemical analysis the inventors have now succeeded in isolating, demonstrating and characterizing human conglutinin.

BRIEF DESCRIPTION OF THE INVENTION

Accordingly, the invention in a first aspect relates to conglutinin which is obtained from human plasma, and has a monomer relative molecular weight, $M_r$, of 40K measured in unreduced state and 66K measured in reduced state by sodium dodecyl sulfate polyacrylamide gel electrophoresis (SDS-PAGE), shows calcium-dependent and sugar inhibitable binding to complement-reacted immune complexes and zymosan, and immunological cross-reaction with chicken and rabbit antibovine conglutinin antibody. Further, the conglutinin of the invention agglutinates alexinated, glutaraldehyde-fixed sheep erythrocytes.

In a second aspect the invention relates to an antiserum or a polyclonal anti-conglutinin antibody raised against said conglutinin.

In a third aspect the invention relates to monoclonal anti-conglutinin antibodies raised against said conglutinin.

In a fourth aspect the invention relates to the use of said conglutinin and its antibodies in research, therapy and diagnosis.

BRIEF DESCRIPTION OF THE DRAWINGS

The invention will be described in details in the following parts of the specification with reference to the attached drawing whereon

DETAILED DESCRIPTION OF THE INVENTION

Figure 1:
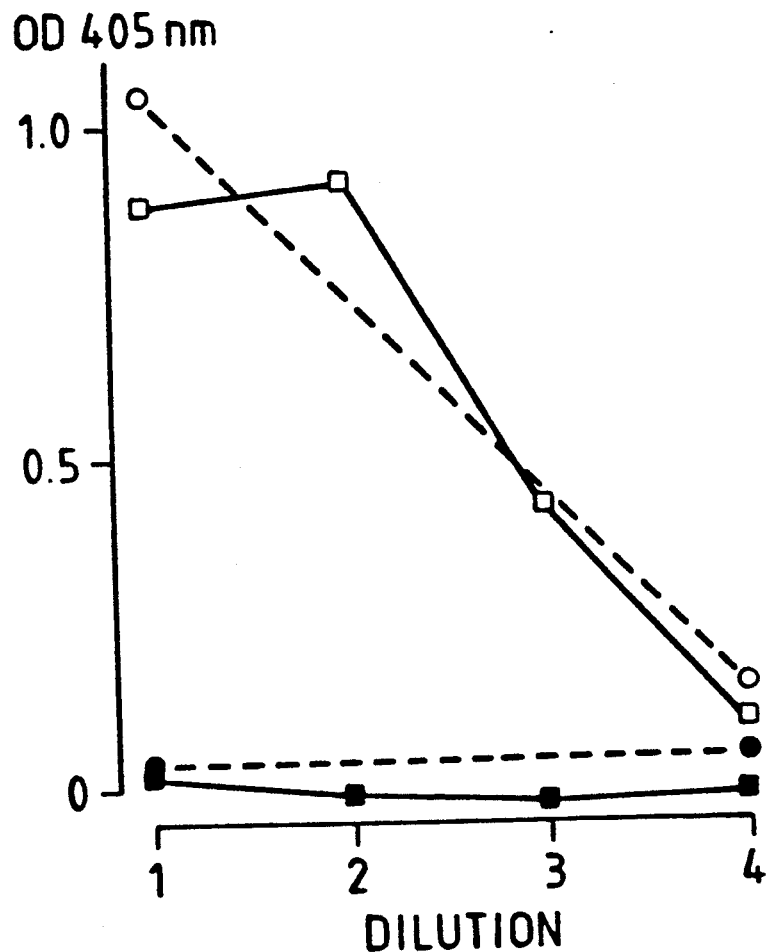
FIG. 1 shows the result of an enzyme immunoassay of human and bovine conglutinin, FIG. 2 the inhibition by various sugars of the binding of the conglutinin of the invention to alexinated immune complexes, FIG. 3 the binding of the human conglutinin to zymosan, FIG. 4 the SDS-PAGE profiles of unreduced human and bovine conglutinin, FIG. 5 the relation between relative molecular weight and mobility of both human and bovine conglutinin, and, FIG. 6 the results of treating conglutinin of the invention with collagenase.

The invention provides for a novel protein, human conglutinin, which is obtainable from human plasma by affinity chromatography with anti-bovine conglutinin antibody coupled to a solid phase.

Said conglutinin is homologous to bovine conglutinin in that it shows a calcium dependent binding to complement reacted immune complexes, and zymosan. The conglutinin of the invention is further homologous to bovine conglutinin in that it shows an immunological cross reaction with both chicken and rabbit anti-bovine conglutinin antibody. Similar to bovine conglutinin the binding of the human conglutinin to complement reacted immune complexes is inhibited with certain sugars, notably N-acetyl-D-glucosamine but not N-acetyl-D-mannoseamine. Also like bovine conglutinin said human conglutinin binds to zymosan in the presence of calcium and is eluted upon addition of ethylenediaminetetraacetic acid (EDTA).

Conglutinin has interesting pharmacological properties in that it is involved in the immune system through its interaction with complement factors and immune complexes.

It is therefore contemplated that human conglutinin may be used in the treatment of disorders in humans in which the complement system is activated, notably disorders such as infections, autoimmune diseases, and cancers.

Conglutinin may also be used extracorporally for the removal from blood or plasma of immune complexes containing complement activation products. This may be done by perfusion of blood or plasma over conglutinin coupled to a solid phase carrier.

Conglutinin may further be used in assays for the determination of immune complexes containing complement activation products.

It is likely that conglutinin deficiencies will be discovered following the possibility of monitoring conglutinin levels in blood provided by the present invention, and purified conglutinin may be used to alleviate such conditions in humans.

Human conglutinin may be used to raise antiserum or polyclonal anti-conglutinin antibodies by immunisation of a host organism with conglutinin and subsequent recovery of the polyclonal antibodies.

For the production of monoclonal antibodies anti-conglutinin antibody producing mammalian cells are as known in the art isolated and fused with myeloma cells to produce clones of cells originating from single fused cells each producing a monoclonal antibody directed against human conglutinin.

Such monoclonal antibodies may be used alone or in combination for the purposes indicated below.

The anti-conglutinin antibodies thus obtained may be used in affinity chromatography for the recovery of conglutinin from human plasma, and for the purification of conglutinin-containing immune complexes.

Anti-conglutinin antibody may further be used for monitoring conglutinin levels in blood, which will provide important information about the biological and physiological functions of conglutinin, and, since conglutinin is consumed during infections, provide means for obtaining information about ongoing formation of immune complexes and activation of the complement system. Decreased levels of conglutinin could further indicate impaired capacity for bacterial clearence.

In rheumatic, inflammatory, and autoimmune diseases, etc. the activation of the complement system is of pathophysiological importance and monitoring the conglutinin level will provide information for the evaluation of disease activity and management.

Immune complexes are currently thought to be involved in the progression of malignant diseases, and may consume conglutinin through activation of complement. Monitoring conglutinin levels in human blood may therefore be of importance in the management of malignant diseases.

Since it has been found that conglutinin levels in blood are lowered at parturition it is also envisaged that monitoring of the conglutinin level during pregnancy may be used to give an early warning of a pathological pregnancy, abortion, or premature birth.

Anti-human conglutinin antibodies may even further be used for the extracorporeal removal from blood or plasma of conglutinin-containing immune complexes.

The protein of the invention, human conglutinin, purified from plasma or produced by gene technology may also be used in reconstituting the activity in patients suffering from diseases associated with lowered conglutinin levels or cases where large amounts are needed to combat the disease.

Human conglutinin was obtained by batch-wise affinity chromatography of human plasma with anti-bovine conglutinin antibody coupled to a cyanogenbromide-activated dextran gel. The beads were treated at room temperature with sodium dodecyl sulfate (SDS) sample buffer containing iodoacetamide, and the eluate subjected to SDS-PAGE on 5 to 20% gradient gels. The proteins were electrophoretically transferred to nitrocellulose, cut into 2 mm strips, incubated with biotinylated anti-bovine conglutinin antibody or biotinylated normal chicken IgG, and subsequently developed with avidin-alkaline phosphatase conjugate substrate, 5-bromo-4-chloroindoxyl phosphate and nitro blue tetrazolium.

BIOLOGICAL CHARACTERIZATION

The ability of human conglutinin to bind to complement reacted immune complexes in the presence of calcium was demonstrated in the Bio-ELISA described later, the results of which are shown in FIG. 1. The wells of a microplate were coated with rabbit IgG, either directly by incubation with rabbit IgG, or indirectly by first coating with bovine serum albumin (BSA) and then rabbit anti-BSA antiserum. The wells were then reacted with complement by incubation at 37° C. with human serum. After wash with EDTA the wells with complement reacted immune complexes were incubated with dilutions of human conglutinin in buffer with EDTA or buffer with calcium. The calcium dependent binding of conglutinin was evaluated by the subsequent application of biotinylated anti-conglutinin antibody followed by enzyme coupled avidin, and measurement of the optical density (OD) at 405 nm. The OD values were corrected for background values obtained from wells incubated with buffer instead of plasma.

In FIG. 1 OD values at 405 nm of microwells coated with rabbit IgG and human complement incubated with two-fold dilutions of human plasma starting at 1/30 (□ and ■) or bovine serum diluted $10^{-4}$ and $10^{-5}$ (○ and ●) in the presence of $Ca^{2+}$ (□ and ○) or EDTA (■ and ●), and assayed for human and bovine conglutinin as indicated above, are presented. The calcium dependence of the binding of both human and bovine conglutinin to complement reacted immune complexes is clearly demonstrated in FIG. 1.

In this assay it has been shown that human conglutinin cross-reacts with antibody raised by the immunization of rabbits and chickens with bovine conglutinin purified from bovine serum, and vice versa that antibody raised against human conglutinin reacts with both bovine and human conglutinin.

Figure 2:
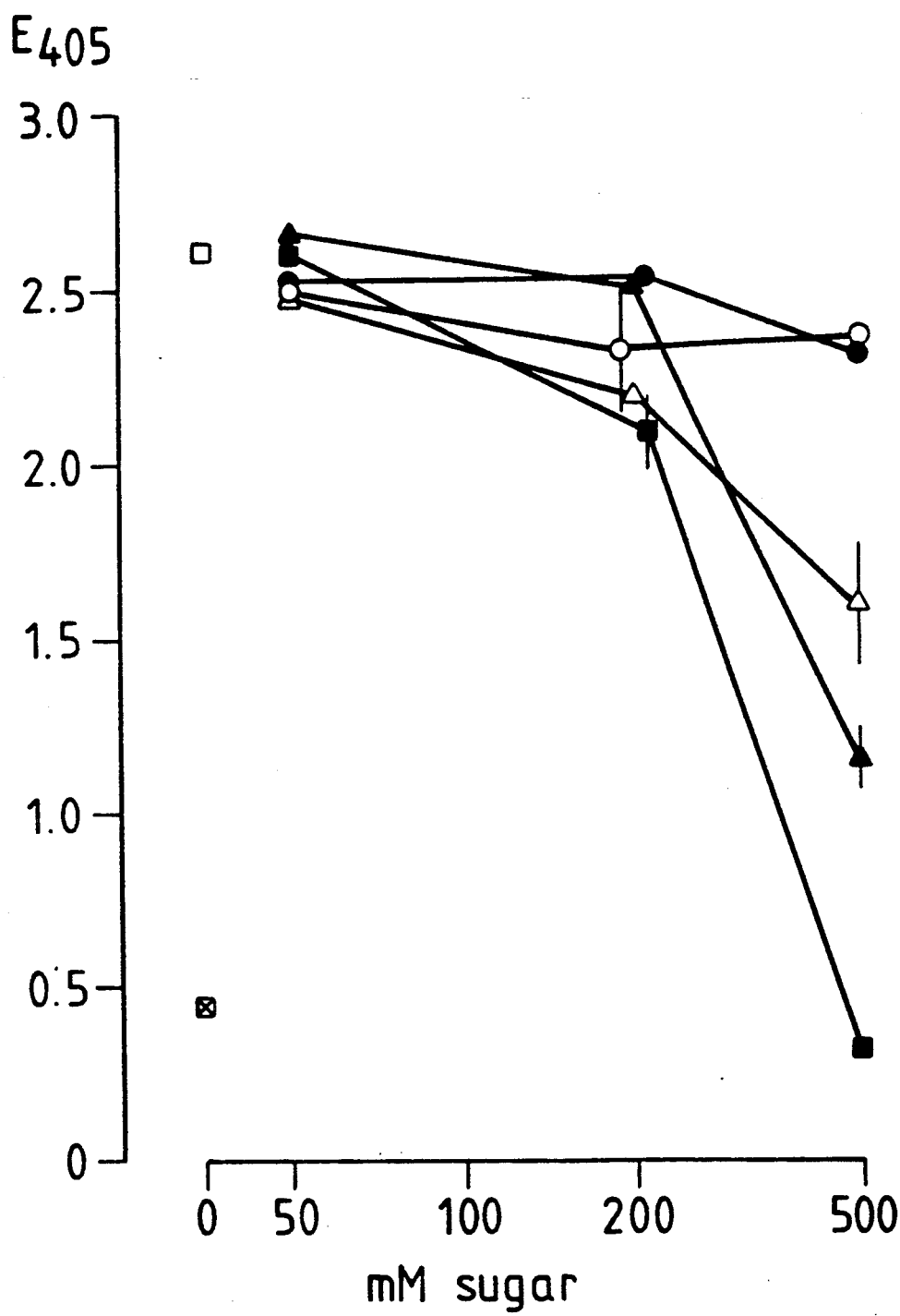

It was also shown that human conglutinin, like bovine conglutinin, is inhibited in its binding to complement reacted immune complexes by certain sugars, notably N-acetyl-D-glucosamine, but not by N-acetyl-D-mannosamine, methyl-α-D-glucopyranoside, methyl-α-D-mannoside or saccharose. L-fucose and D-mannose also gave some inhibition as shown in FIG. 2, where the results of tests in which microwells coated with normal rabbit IgG and reacted with human serum were incubated with human plasma diluted 1:100 in $Ca^{2+}$-Tween-sodium barbital buffer (VB) containing various concentrations at N-acetyl-D-glucosamine (■), glucose (●), N-acetyl-D-mannosamine (○), L-fucose (▲) and D-mannose (△). The results of incubation without sugars in $Ca^{2+}$-Tween-VB buffer (□) and in EDTA-Tween-VB (■) are also shown.

Figure 3:
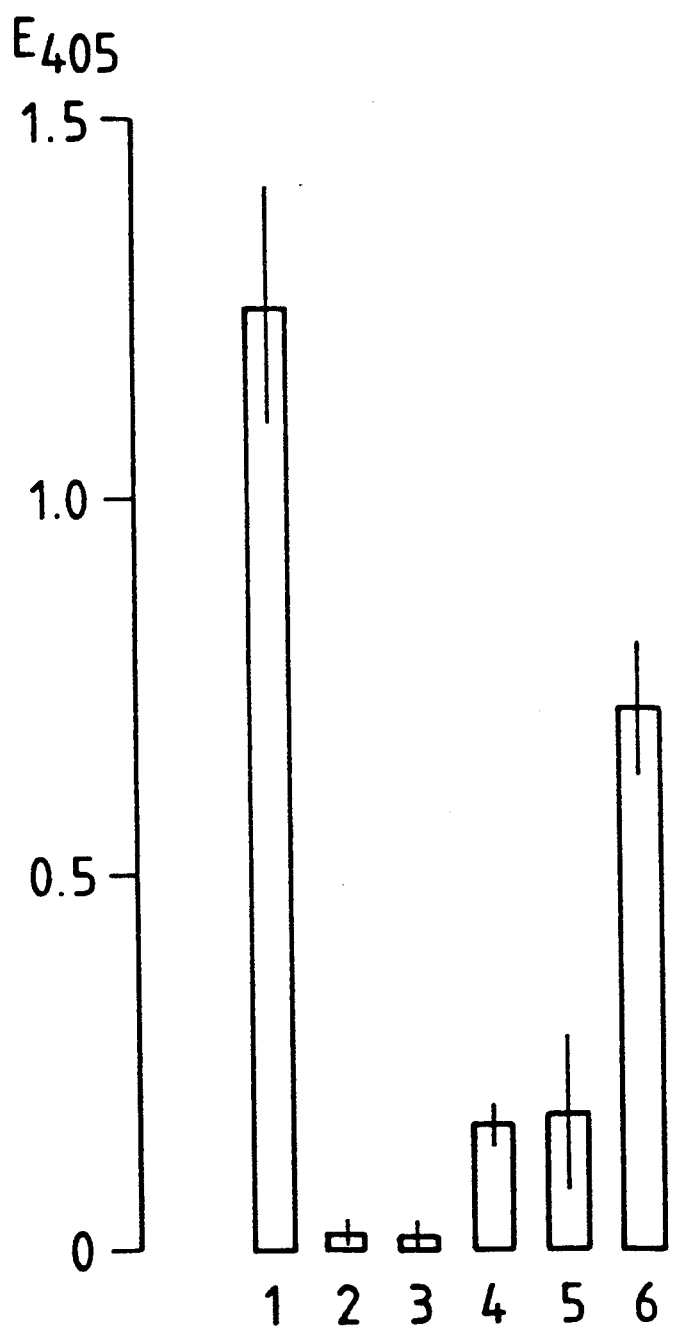

Further, it was shown that similarly to bovine conglutinin also human conglutinin binds to zymosan in the presence of calcium, and is eluted upon addition of EDTA, as shown in FIG. 3.

In FIG. 3 the results of a test in which heparinized freshly drawn plasma from a donor with high activity in the conglutinin assays was incubated with zymosan in $Me^{2+}$(Ca 2 mM, Mg 1 mM)-VB. Suspensions were centrifuged (1700 × g, 20 min.) and the supernatant collected, and subsequently measured in the Bio-ELISA described hereinafter at 1:60 dilution.

In the figure a comparison is seen between (1) the heparinized plasma, (2) the supernatant after incubating zymosan with plasma, (3–5) the supernatant from washing the zymosan and (6) the EDTA eluate.

Conglutinating activity with alexinated erythrocytes has not been demonstrated in human serum. In order to show the activity in human plasma it proved necessary to glutaraldehyde-fix the sheep erythrocytes before alexinating with antibody and complement. With such erythrocytes conglutinating activity may be demonstrated in human plasma with high conglutinin content as judged by the two ELISA methods, Ag-ELISA and Bio-ELISA described below.

PHYSICAL-CHEMICAL CHARACTERIZATION

The structural relationship between bovine and human conglutinin was demonstrated by the induction of the production of cross-reacting antibody upon immunization. The cross-reaction was revealed in the above biological assay, and also in a purely immunochemical ELISA (Ag-ELISA described below), where microwells coated with F(ab')$_2$ fragments of said antibodies were incubated with dilutions of human plasma or serum, and developed with biotin-labelled anti-conglutinin antibody and enzyme coupled avidin. Antibodies from chickens and rabbits were used in various combinations with identical results.

SDS-PAGE

Human conglutinin purified as above was fractionated by SDS-PAGE in the presence of 10 mM iodoacetamide and in the absence of reducing agents.

Figure 4:

The proteins were transferred to nitrocellulose by Western blotting, and developed by incubation with biotinylated antibody against bovine conglutinin and enzyme coupled avidin. The same procedure was repeated using bovine conglutinin. The results are presented in FIG. 4. In FIG. 4 it is clearly seen that from the human conglutinin two main bands were developed. The relative molecular weights ($M_r$) of these unreduced bands were 40 K and 330 K, respectively, as estimated from a standard curve constructed using reduced and alkylated myosin, β-galactosidase, BSA, ovalbumin, and β-lactoglobulin.

From bovine conglutinin six main bands were developed indicating that it exists in polymeric forms from monomer to hexamer, whereas the two bands from human conglutinin indicates the existence of a monomer and a hexamer.

Figure 5:
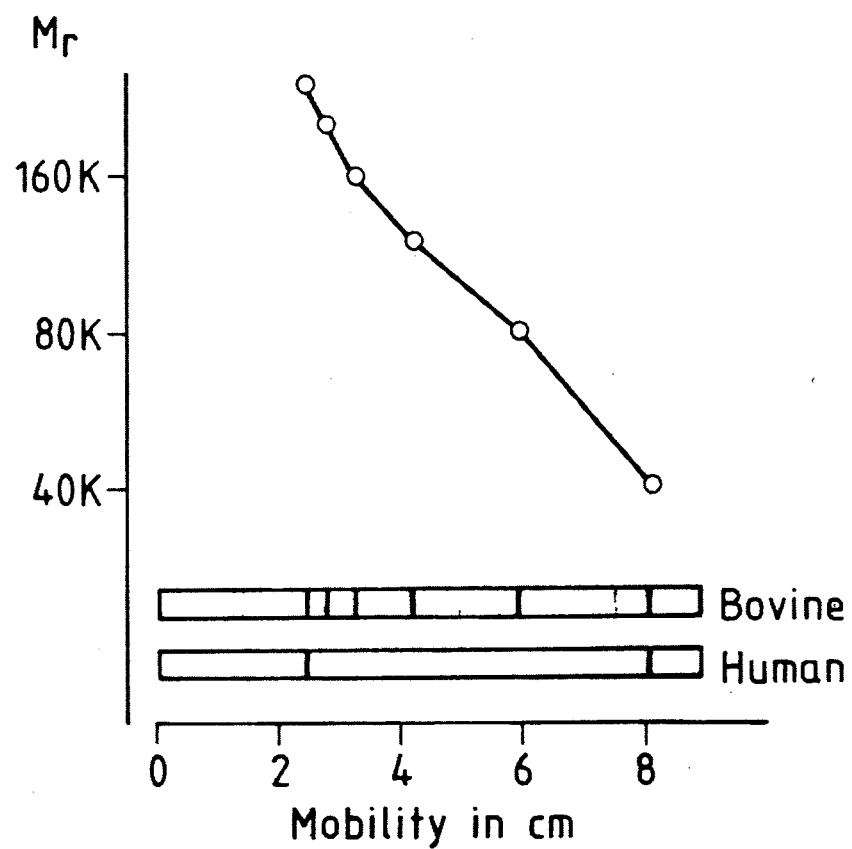

In FIG. 5 the mobilities of the six main bands from bovine conglutinin is plotted on semi-logarithmic scale against relative molecular weight assuming that they represent monomer, dimer, trimer, tetramer, pentamer, and hexamer, respectively. The two bands from human conglutinin showed a slightly lower mobility than the corresponding bovine bands, but have in FIG. 5 been aligned with the bovine blot to emphasize the similarity.

Figure 6:
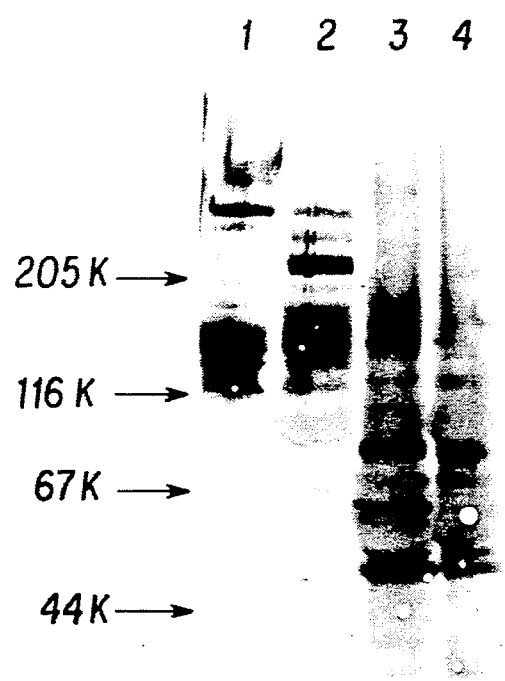

In FIG. 6 it is demonstrated that human conglutinin (like bovine conglutinin) is sensitive to treatment with the protease collagenase.

In FIG. 6 lane 1 representing unreduced material eluted from beads incubated with human plasma, a major band at 330 K is seen. In lane 3 the eluted material similar to in lane 1 was reduced and alkylated. One major band at 66 K is seen along with two minor bands at 90 K and 45 K.

Lane 2 shows the immunochemical staining of material from collagenase treated beads. The 330 K band seen with the unreduced beads (lane 1) has been reduced and a distinct band at 240 K has appeared.

Collagenase treatment followed by reduction and alkylation gives the staining pattern seen in lane 4. The 66 K band seen with the reduced and alkylated non-collagenase treated material (lane 3) has disappeared.

TABLE 1

| AMINO ACID COMPOSITION* | |
|---|---|
| Amino Acid | Molar % |
| Asp | 1.2 |
| Glu | 1.8 |
| Ser | 6.0 |
| Gly | 13.0 |
| His | 1.6 |
| Arg | 6.9 |
| Thr | 5.1 |
| Ala | 3.5 |
| Pro | 5.7 |
| Tyr | 3.2 |
| Val | 6.5 |
| Met | 1.5 |
| Cys | 10.1 |
| Ile | 6.5 |
| Leu | 18.0 |
| Phe | 4.5 |
| Lys | 4.8 |

*Data shown are for human conglutinin protein in monomeric (reduced state) form.

MONOCLONAL ANTIBODIES

Furthermore, the human conglutinin was identified by the use of monoclonal antibodies. The protein was isolated from human plasma as described above by affinity chromatography on Sepharose 4B coupled chicken anti-bovine conglutinin followed by SDS-PAGE and Western blotting onto nitrocellulose. The 330 K band was localized by immuno staining strips cut from the sides of the nitrocellulose sheet, and the area comprising the 330 K band was cut out from the sheet, homogenized and emulsified with complete Freund's adjuvant before injection into Balb/c mice. After booster injections spleens were taken and the lymphocytes fused with X63-Ag 8653 myeloma cells (Kearney et al., J. Immunol. 123 (1979) pp. 1548-1550). After culture and cloning hybridomas were isolated which produce antibody reacting with the protein identified as human conglutinin by the use of the cross-reacting antibodies. Monoclonal antibodies thus obtained 1) reacted with complement coated ELISA plates which were incubated with human plasma with a high conglutinin titer (as judged by zymosan agglutination) in the presence of calcium ions, but not if instead of calcium ions EDTA was present, 2) this binding in the presence of calcium was inhibitable with N-acetyl-D-glucosamine 3) showed no reaction if serum instead of plasma was used, 4) when coupled to Sepharose 4B they could remove from plasma the 330 K protein with which the anti-bovine conglutinin reacts, 5) when biotinylated and used as second antibody in the Ag-ELISA below they identify the same human plasma as high and low in conglutinin as does the biotinylated anti-bovine conglutinin, 6) the 330 K band was stained when Western blots of partially purified human conglutinin were incubated first with the monoclonal antibodies and subsequently with enzyme-labelled rabbit anti-mouse immunoglobulin.

The fact that the monoclonal antibodies referred to above do not bind to the human conglutinin of the invention in serum is not a positive indication that human conglutinin is not present in serum, but indicates that human conglutinin present in serum must have a configuration different from its configuration in plasma.

Human conglutinin may be produced as indicated above and examplified below by isolation and purification from human serum or plasma.

It is also anticipated that human conglutinin eventually may be synthesized by any method for the synthesis of polypeptides known to those skilled in the art.

A summary of such techniques may be found in J. M. Stewart and J. D. Young, Solid Phase Peptide Synthesis, W. H. Freeman, San Francisco, 1969 and J. Meienhofer, Hormonal Proteins and Peptides, Vol. 2, (1973), p. 46, Academic Press, New York, for solid phase synthesis, and in E. Schroder and K. Lubke, The Peptides, Vol. 1, (1965), Academic Press, New York, for classical solution synthesis.

Further, it is contemplated that human conglutinin may be produced by recombinant DNA technology.

Human conglutinin may be presented as pharmaceutical compositions and administered to humans in analogy with known methods. Conglutinin may be administered perorally, topically, rectally, vaginally, intravenously, intramuscularily, intrathecally or subcutaneously at dosages in the range of from about 1 to 1000 µg/kg body weight, although a lower or higher dosage may be administered. The required dosage will depend on the severity of the condition of the patient, the peptide used, the mode of administration, and the duration of treatment.

The compositions may be formulated in the form of slow-release or depot preparations.

For the purpose of parenteral administration, conglutinin is dissolved in sterile, isotonic saline solutions, optionally in combination with physiologically compatible, inert carriers or fillers.

ELISA FOR CONGLUTININ EPITOPES (Ag-ELISA)

Microplates (Immunoplate II, Nunc) were incubated overnight at room temperature with 200 µl of F(ab')2-fragments of chicken-antibovine conglutinin at 1 µg/ml 0.1M hydrogen carbonate buffer per well. The wells were washed three times in Tween-phosphate buffered saline (PBS) (0.05% v/v Tween). Test material was diluted in Tween-EDTA-phosphate buffered saline (PBS) (0.05% Tween and 10 mM EDTA) and 200 µl was added in duplicate to the plate which was incubated for 2 hours at room temperature. The plate was washed three times in Tween-PBS and 200 µl of biotinylated rabbit-anti-bovine conglutinin (500 ng/ml Tween-PBS) was added and incubation continued overnight at 4° C. The plate was washed three times and avidin alkaline phosphatase ($2.2 \times 10^{-2}$ U/ml Tween-PBS) was added. After 2 hours of incubation at room temperature and wash, substrate 4-nitrophenylphosphate (PNPP) was added to the wells at 1 mg/ml diethanolamine (DEA) buffer. Optical density was read at $E_{405}$ (Immunoreader NJ-2000, Intermed, Nippon, Tokyo, Japan) after incubation at 37° C. in the dark. In all tests a dilution series of a conglutinin positive human plasma was included as standard. This plasma was arbitrarily assigned a conglutinin activity of 1000 units per ml.

ELISA FOR BIOLOGICAL CONGLUTININ ACTIVITY (BIO-ELISA)

Microwells were incubated overnight at room temperature with 200 µl of normal rabbit IgG at 10 µg/ml tris buffered saline (TBS) and washed three times in Tween-PBS. Subsequent complement attachment was found more efficient when the primary IgG coating was in TBS than when hydrogen carbonate buffer was used. Normal donor serum diluted 10 fold in $Me^{2+}$ (2 mM Ca, 1 mM Mg) - veronal buffer (VB) (4 mM sodium barbital 0.145M NaCl) was added and complement coating proceeded for 3 hours at 37° C. A low binding of conglutinin was achieved also when the serum-incubation was excluded, probably due to activation of complement in the test plasma. The wells were washed twice in Tween-EDTA-VB (VB containing 10 mM EDTA and 0.05% Tween) buffer and once in $Me^{2+}$-Tween-VB buffer. The test samples were added at appropriate dilution in $Me^{2+}$-Tween-VB or EDTA-Tween-VB. After incubation for 4 hours at room temperature the wells were washed three times. Two hundred µl of biotin-labelled rabbit antibovine conglutinin, (1 µg/ml $Me^{2+}$-Tween-VB buffer) was added and incubated overnight at 4° C. The plates were further treated as described for the Ag-ELISA.

The two ELISA assays described above were used extensively in the characterization of the human conglutinin of the invention and the results of their application has been referred to in the preceding parts of this specification including the drawing.

The invention will be further illustrated in the following example. The example is intended only for illustration and is not intended to limit the scope of the invention in any way

EXAMPLE 1

Isolation and Purification of Human Conglutinin

1) Human blood is collected in anticoagulant (e.g. 1/10 vol. of phosphate-buffered citrate-dextrose or EDTA)

2) Plasma is recovered from blood selected for high conglutinin content by centrifugation after incubation of the blood for ½ to 1 hour at 37° C. (The vol. of plasma is in the following referred to as "1 vol.". Unless otherwise indicated the procedures are carried out at room temperature).

3) Salt fractionation

Conglutinin is purified by precipitation with salt (e.g. 1M ammonium sulphate, or 8% sodium sulphate) or polyethylene glycol (PEG) (e.g. PEG 6000 at 6% (w/v)). The precipitate is collected by centrifugation ($10^4$ g, 20 minutes) and washed twice with the precipitating solution. The washed precipitate is taken up in a small volume (e.g. 1/20 vol.) of water or buffered saline and dialyzed against buffered saline (e.g. PBS or TBS).

4) Delipidation

The dialysate is centrifuged 1 hour at $10^5$ g, 25° C., to remove insoluble material and lipid. The efficacy of lipid removal may be improved increasing the density of the solution before centrifugation, e.g. by adjusting the solution to 1M NaCl, 10% sucrose and overlaying with a small vol. of buffered saline in which the lipid will accumulate.

Alternatively, lipid may be removed by extraction with organic solvent (e.g. Frigen, Hoechst/Behringwerke) by treatment of either the plasma or the precipitated material.

5) Removal of contaminating fibronectin

The molarity of NaCl is adjusted to 1M and the solution passed through a column of insolubilized gelatin (e.g. 1/10 vol. of Sepharose-coupled gelatin). The column is washed with further 1/10 vol. of phosphate buffered 1M NaCl with 10 mM EDTA. The effluent is pooled. The effluent is dialyzed against buffered saline.

The affinity of conglutinin for fibronectin in isotonic saline may be explored through purification by affinity chromatography on solid phase fibronectin.

6) Affinity purification on solid phase carbohydrates

The resolubilized, clarified precipitate is treated with zymosan by incubation with stirring for 1 hour with 1/10 vol. of a 50% suspension of zymosan in PBS, 10 mM $CaCl_2$. The zymosan is sedimented (2000 g, 20 minutes) and washed 4 times with 1 vol. of PBS/$CaCl_2$. The conglutinin is released by resuspending the zymosan in 1/10 vol. of PBS, 10 mM EDTA and incubating (lo minutes) before removing the zymosan by centrifugation (7000 g, 15 minutes).

The supernatant containing conglutinin is dialyzed (against PBS or TBS), and the binding to zymosan and release with EDTA is repeated.

Agarose or N-acetyl-D-glucosamine substituted agarose may be used instead of zymosan, in which case the purification may be carried out by column chromatography.

7) Affinity purification with anti-conglutinin antibody

Anti-conglutinin is insolubilized (e.g. by coupling to CNBr-activated Sepharose ®). The partly purified conglutinin is treated with the insolubilized anti-conglutinin either batch-wise or on a column. The matrix is washed and the conglutinin eluted by treatment with partially denaturing reagent (e.g. 0.1M glycine, pH 2.4; 3M KSCN; 0.1M diethylamine, pH 11).

8) Gel chromatography

The conglutinin is further purified by gel chromatography (e.g. on Sephacryl ® S500) in EDTA containing buffered saline which may in addition contain a low concentration of SDS (e.g. 0.2%).

9) Ion exchange chromatography

The purity of the conglutinin may be further improved by ion exchange chromatography. DEAE Sepharose ® and Mono-Q ® beads have proved useful.

The conglutinin was eluted with a NaCl gradient in 10 mM phosphate.

The product was characterized as indicated above, and shown to be human conglutinin.

I claim:

1. A method of treating disorders in human subjects, wherein said disorders cause a conglutinin deficiency, said method comprising the administration to said human subjects of therapeutically effective amounts of human conglutinin in substantially pure form comprising a plasma protein of monomeric molecular weight of 40,000 daltons in the unreduced state and 66,000 daltons in the reduced state, and a polymeric relative molecular weight of 330,000 daltons in the unreduced state, said protein comprising in the monomeric reduced state the following amino acid composition:

| Amino Acid | Molar % |
| --- | --- |
| Asp | 1.2 |
| Glu | 1.8 |
| Ser | 6.0 |
| Gly | 13.0 |
| His | 1.6 |
| Arg | 6.9 |
| Thr | 5.1 |
| Ala | 3.5 |
| Pro | 5.7 |
| Tyr | 3.2 |
| Val | 6.5 |
| Met | 1.5 |
| Cys | 10.1 |
| Ile | 6.5 |
| Leu | 18.0 |
| Phe | 4.5 |
| Lys | 4.8; | said protein exhibiting calcium-dependent and sugar-inhibitable binding to complement-reacted immune complexes and zymosan, and said protein being sensitive to collagenase digestion.

2. A method of treating human subjects for microbial infections, wherein said microbial infections cause a conglutinin deficiency, said treating comprising the administration to said human subjects of therapeutically effective amounts of human conglutinin in substantially pure form comprising a plasma protein of monomeric molecular weight of 40,000 daltons in the unreduced state and 66,000 daltons in the reduced state, and a polymeric relative molecular weight of 330,000 daltons in the unreduced state, said protein comprising in the monomeric reduced state the following amino acid composition:

| Amino Acid | Molar % |
| --- | --- |
| Asp | 1.2 |
| Glu | 1.8 |
| Ser | 6.0 |
| Gly | 13.0 |
| His | 1.6 |
| Arg | 6.9 |
| Thr | 5.1 |
| Ala | 3.5 |
| Pro | 5.7 |
| Tyr | 3.2 |
| Val | 6.5 |
| Met | 1.5 |
| Cys | 10.1 |
| Ile | 6.5 |
| Leu | 18.0 |
| Phe | 4.5 |
| Lys | 4.8; | said protein exhibiting calcium-dependent and sugar-inhibitable binding to complement-reacted immune complexes and zymosan, and said protein being sensitive to collagenase digestion.

3. The method of claim 2 wherein said administration is prophylactic.

4. The method of claim 2 wherein said administration is ameliorative.

5. The method of claim 2 wherein said administration is curative.

6. A method of treating human subjects with conglutinin deficiencies, said treatment to restore normal levels of conglutinin, comprising the administration to said human subjects of therapeutically effective amounts of human conglutinin in substantially pure form comprising a plasma protein of monomeric molecular weight of 40,000 daltons in the unreduced state and 66,000 daltons in the reduced state, and a polymeric relative molecular weight of 330,000 daltons in the unreduced state, said protein comprising in the monomeric reduced state the following amino acid composition:

| Amino Acid | Molar % |
|---|---|
| Asp | 1.2 |
| Glu | 1.8 |
| Ser | 6.0 |
| Gly | 13.0 |
| His | 1.6 |
| Arg | 6.9 |
| Thr | 5.1 |
| Ala | 3.5 |
| Pro | 5.7 |
| Tyr | 3.2 |
| Val | 6.5 |
| Met | 1.5 |
| Cys | 10.1 |
| Ile | 6.5 |
| Leu | 18.0 |
| Phe | 4.5 |
| Lys | 4.8; | said protein exhibiting calcium-dependent and sugar-inhibitable binding to complement-reacted immune complexes and zymosan, and said protein being sensitive to collagenase digestion.

* * * * *